US010987193B2

(12) United States Patent
Chen

(10) Patent No.: US 10,987,193 B2
(45) Date of Patent: Apr. 27, 2021

(54) CLAMPING DEVICE

(71) Applicant: HIWIN TECHNOLOGIES CORP., Taichung (TW)

(72) Inventor: Yen-Chun Chen, Taichung (TW)

(73) Assignee: Hiwin Technologies Corp., Taichung (TW)

(*) Notice: Subject to any disclaimer, the term of this patent is extended or adjusted under 35 U.S.C. 154(b) by 291 days.

(21) Appl. No.: 16/268,859

(22) Filed: Feb. 6, 2019

(65) Prior Publication Data
US 2020/0246111 A1 Aug. 6, 2020

(51) Int. Cl.
A61B 90/57 (2016.01)
F16B 2/14 (2006.01)
A61G 13/10 (2006.01)

(52) U.S. Cl.
CPC ............ A61B 90/57 (2016.02); A61G 13/101 (2013.01); F16B 2/14 (2013.01); A61B 2090/571 (2016.02)

(58) Field of Classification Search
CPC ..... A61B 90/57; A61B 2090/571; F16B 2/14; F16B 2/12; A61G 7/1078; A61G 7/0507; A61G 7/0508; A61G 7/0514; A61G 13/101; F16M 13/022; H02B 1/052; H01R 9/2608
USPC ... 248/316.2, 316.4, 220.21, 229.12, 229.22, 248/228.3, 231.41
See application file for complete search history.

(56) References Cited

U.S. PATENT DOCUMENTS

| 7,003,827 | B2* | 2/2006 | DeMayo | A61G 13/10 248/229.14 |
| 8,485,509 | B2* | 7/2013 | Wang | B24B 41/06 269/249 |
| 9,022,334 | B1* | 5/2015 | DeMayo | F16M 13/022 248/229.22 |
| 9,585,806 | B2* | 3/2017 | Herrig | A61G 13/101 |
| 10,531,733 | B1* | 1/2020 | Ho | F16M 13/022 |
| 10,716,726 | B2* | 7/2020 | Bergman | A61G 7/05 |
| 10,874,571 | B2* | 12/2020 | Zahynacz | F16B 2/185 |
| 2012/0126079 | A1* | 5/2012 | Russell | A61G 13/101 248/229.23 |
| 2012/0260923 | A1* | 10/2012 | Campagna | A61F 5/37 128/845 |

* cited by examiner

Primary Examiner — Robert G Santos
Assistant Examiner — Rahib T Zaman
(74) Attorney, Agent, or Firm — Muncy, Geissler, Olds & Lowe, P.C.

(57) ABSTRACT

A clamping device includes a support base, a handle pivoted to the support base, a clamping unit including an upper jaw, a lower jaw and a slide respectively mounted in the support base, and a locking unit including a stop block and a locking bar respectively mounted in the support base. When the handle is pressed, the locking bar is driven to unlock the stop block for allowing movement of the slide, and then the slide is pushed by the handle to lift the lower jaw, causing the upper jaw and the lower jar block to clamp a side rail of an operating bed. When the handle is returned, the stop block is locked by the locking bar, so that the slide is positioned to prevent accidental loosening.

10 Claims, 14 Drawing Sheets

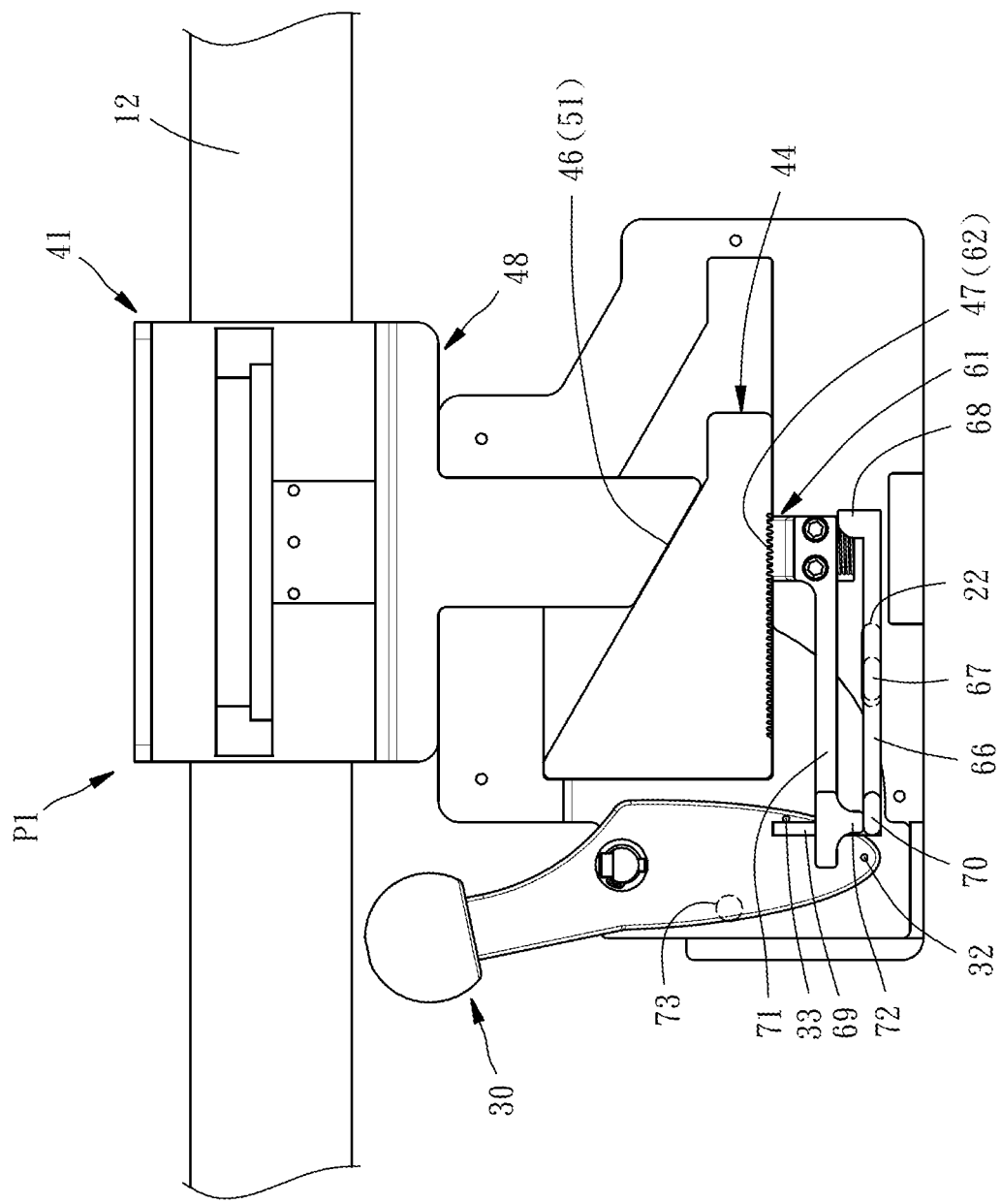

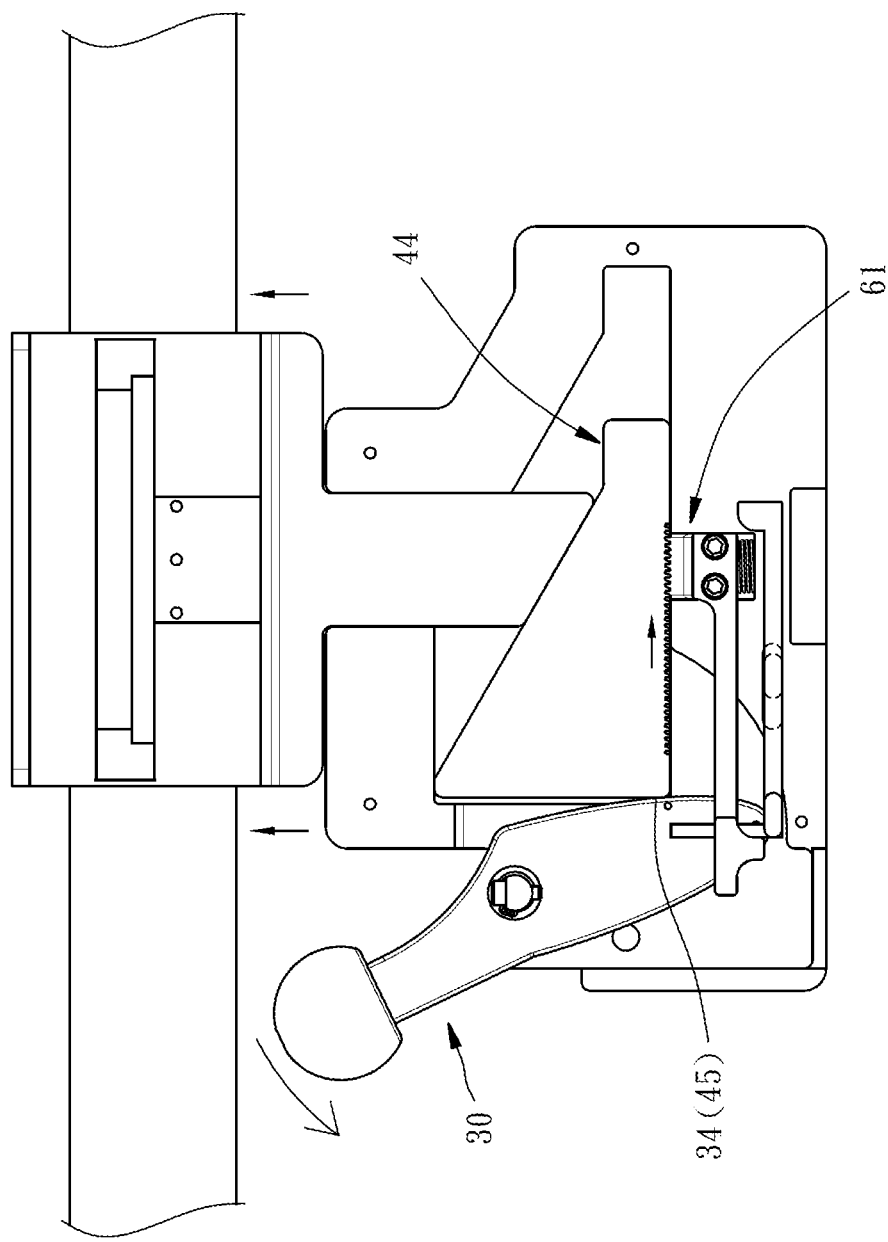

CLAMPING DEVICE

BACKGROUND OF THE INVENTION

1. Field of the Invention

The present invention relates to clamp technology and more particularly, to a clamping device, which is quick to locate and convenient to assemble and disassemble.

2. Description of the Related Art

Before the surgery, the surgical auxiliary device (such as the robotic arm) is usually placed on the bedside of the operating bed by a clamp, so that the surgeon can perform the operation in a more efficient manner with the assistance of the aforementioned surgical auxiliary device.

In the prior art related to operating bed clamp, there is a way to lock the clamp to the bedside of the operating bed by a knob, which makes disassembly and assembly very time consuming and laborious. Further, U.S. Pat. No. 7,003,827 discloses an operating table support clamp. In addition to the problems of complicated operation and inconvenient assembly, this design is lack of a safety mechanism. It is easy to be accidentally dropped by the surrounding people.

SUMMARY OF THE INVENTION

The present invention has been accomplished under the circumstances in view. It is the main object of the present invention to provide a clamping device, which is quick to locate and convenient to disassemble and ensures high application safety.

To achieve this and other objects of the present invention, a clamping device comprises a support base, a handle, a clamping unit and a locking unit. The handle is pivotally mounted to one end of the support base. The clamping unit comprises an upper jaw, a slide and a lower jaw. The upper jaw is affixed to the top surface of the support base. The slide is mounted in the support base and horizontally movable relative to the support base by the handle, comprising a first positioning portion and a slope. The lower jaw is vertically movably mounted to the support base, comprising a slope. The slope of the lower jaw is abutted against the slope of the slide so that the lower jaw is upwardly movable by the slide from a release position to a clamping position where the side rail is clamped between the upper jaw and the lower jaw. The locking unit comprises a stop block, a return spring and a locking bar. The stop block is vertically movably mounted in the support base, comprising a second positioning portion. The second positioning portion of the stop block incorporates the first positioning portion of the slide. The return spring acts on the stop block to push the stop block toward the slide. The locking bar is horizontally movably mounted in the support base and movable by the handle relative to the stop block between a locking position where a locking portion of the locking bar pushes the stop block to hold the slide in position and an unlocking position where the locking portion of the locking bar is released from the stop block for allowing the slide to be displaced horizontally. At this time, since the side rail is clamped between the upper jaw and the lower jaw, the user can lift the clamping device up to enable the side rail to push the lower jaw downward, such that the slide is pushed to the left by the lower jaw, resulting in that the side rail can be released when the lower jaw is lowered to the release position.

Thus, the clamping device of the present invention is installed and disassembled with one hand and has a safety mechanism to avoid accidental loosening caused by accidental contact by others, thereby achieving rapid positioning, convenient disassembly and application safety.

Preferably, the side rail has an outer surface, and the handle is pivotally connected to the support base with a pivot axle. The axial direction of the pivot axle is perpendicular to the extending direction of the outer surface of the side rail so that the operation direction of the handle is prevented from interfering with the surrounding person or object, enhancing operation convenience.

Preferably, the handle has an arched push surface, and the slide has a bearing plane. Thus, when the handle is pressed, the bearing plane of the slide is pushed by the arched push surface of the handle, causing the handle to steadily and smoothly push the slide.

Preferably, the handle comprises a first lateral portion and a second lateral portion respectively located on one side thereof. The length of the first lateral portion is less than the length of the second lateral portion. The position of the first lateral portion is lower than the position of the second lateral portion. The locking bar has the locking portion located at one end thereof, and an upright portion and a pushing portion located at an opposite end thereof. When the pushing portion of the locking bar is pushed by the first lateral portion of the handle, the locking bar is moved from the locking position toward the unlocking position. When the upright portion of the locking bar is pushed by the second lateral portion of the handle, the locking bar is moved from the unlocking position toward the locking position.

Preferably, the support base comprises an elongated slot, and the locking bar comprises a dial portion located at one end thereof perpendicular to the upright portion. The dial portion of the locking bar is horizontally movably inserted through the elongated slot of the support base and protrudes from one side of the side rail back to the support base, facilitating unlocking by an operator by one hand.

Preferably, the support base further comprises an opening, and the stop block comprises an extension portion engaged into the opening of the support base. The locking unit further comprises a linkage rod stopped against one side of the support base opposite to the side rail. The linkage rod has one end thereof affixed to the extension portion of the stop block, and an opposite end thereof provided with a protrusion. When the locking bar is in the locking position, the dial portion of the locking bar pushes the protrusion of the linkage rod to work as a secondary security mechanism. When the locking bar is in the unlocking position, the protrusion of the linkage rod is released from the dial portion of the locking bar so that the stop block allows the slide to displace.

Preferably, the support base has a magnet mounted therein, and the handle has a notch adapted for receiving the magnet. When the notch of the handle is attached onto the magnet, the handle is attracted and positioned by the magnet, avoiding malfunction of the handle.

Other advantages and features of the present invention will be fully understood by reference to the following specification in conjunction with the accompanying drawings, in which like reference signs denote like components of structure.

BRIEF DESCRIPTION OF THE DRAWINGS

FIGS. 6a-6g are similar to FIG. 3, showing the operation flow of the clamping device.

DETAILED DESCRIPTION OF THE INVENTION

Figure 1:
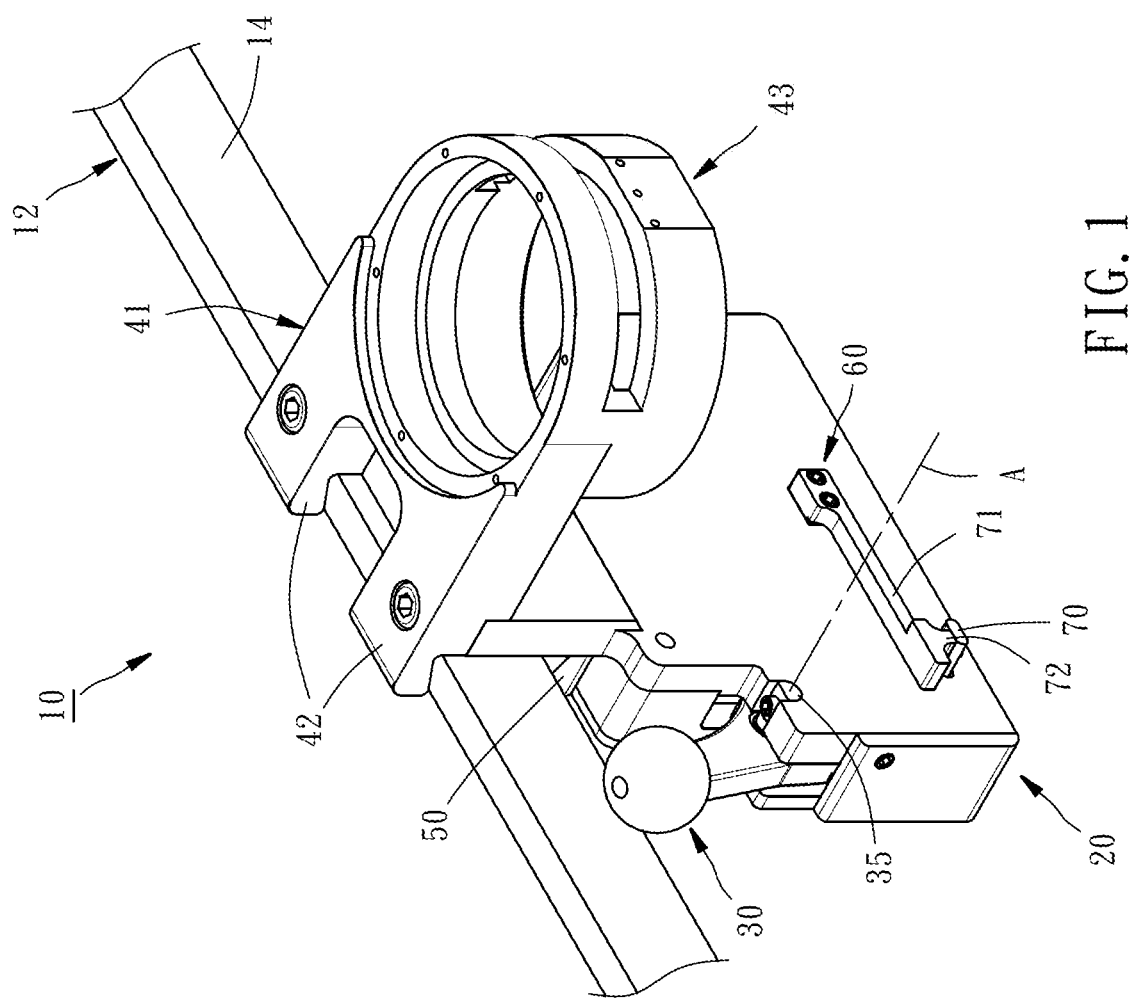
FIG. 1 is an oblique top elevational view illustrating a clamping device affixed to a side rail in accordance with the present invention.

The applicant first declares here, in the entire specification, including the preferred embodiment described below and the clamps of the present invention, the directional terms such as "upper", "lower", "left", "right", "top", "bottom", "inside" and "outside" are based on the direction in the drawings. In the following preferred embodiment, the same reference numerals are used to refer the same or similar elements or structural features thereof.

Referring to FIGS. 1-5, a clamping device 10 includes a support base 20, a handle 30, a clamping unit 40 and a locking unit 60.

The support base 20 is constructed of a front baffle 21 and a back baffle 23. The front baffle 21 has a position-limiting groove 22 located on an inner surface thereof. The back baffle 23 has an elongated slot 24 disposed near one end and cut through the opposing inner and outer surface thereof, and an opening 25 located in the middle and cut through the opposing inner and outer surface thereof.

The handle 30 is pivotally connected to one end of the support base 20 with a pivot axle 35, having a notch 31 located on one side thereof to face toward the front baffle 21, a first lateral portion 32 and a second lateral portion 33 extending from an opposite side thereof toward the back baffle 23, and an arched push surface 34 disposed adjacent to the second lateral portion 33. The length of the first lateral portion 32 is less than the length of the second lateral portion 33, and the position of the first lateral portion 32 is lower than the position of the second lateral portion 33.

The clamping unit 40 comprises an upper jaw 41, a slide 44 and a lower jaw 48.

The upper jaw 41 is affixed to the top side of the back baffle 23 by using fastening members such as screws, having a pair of upper clamping portions 42 located at one end thereof and a mounting seat 43 located at an opposite end thereof for the mounting of a surgical auxiliary device (such as robotic arm, not shown).

Figure 9:
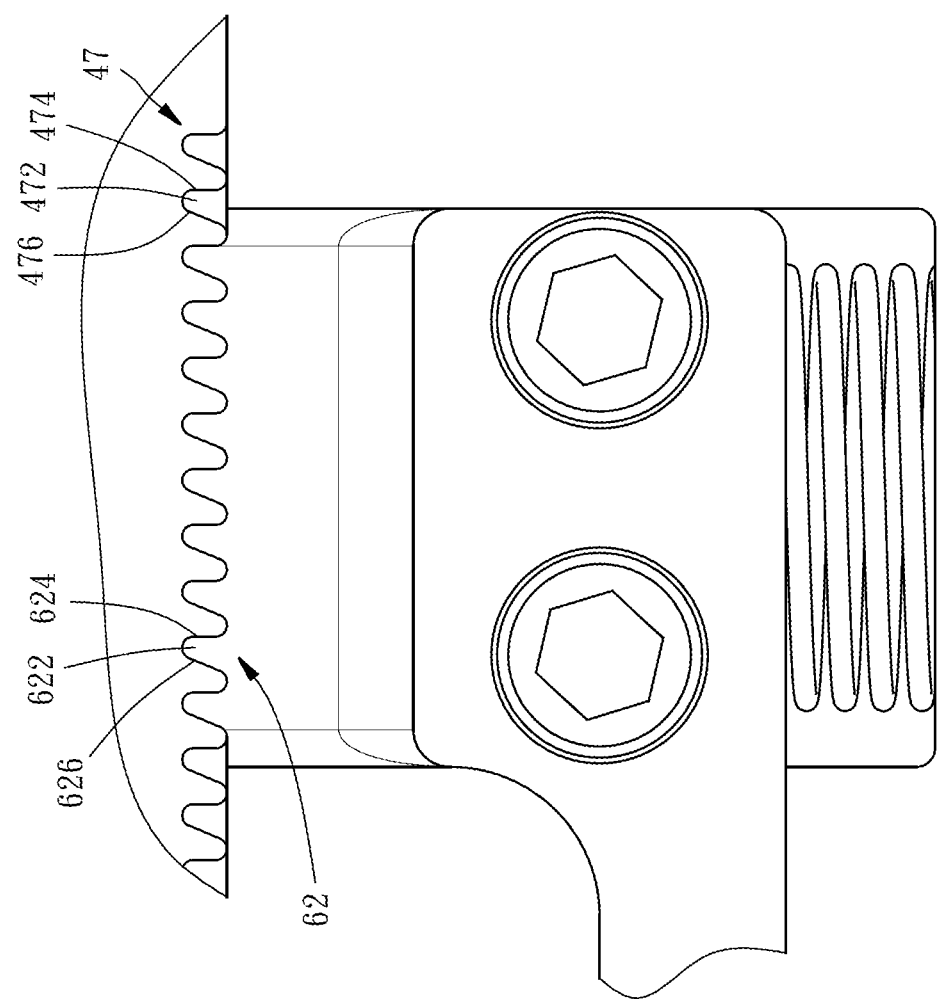
FIG. 9 is an enlarged view of a part of the clamping device, showing the structural relationship between the first positioning portion of the slide and the second positioning portion of the stop block.

The slide 44 is mounted in the support base 20, having a bearing plane 45. When the bearing plane 45 of the slide 44 is pushed by the arched push surface 34 of the handle 30, the slide 44 will produce a horizontal displacement relative to the support base 20. Further, the top surface of the slide 44 forms a slope 46, and the bottom surface of the slide 44 has a first positioning portion 47. In this embodiment, as shown in FIG. 9, the first positioning portion 47 is formed by a plurality of grooves 472 arranged at equal intervals, and the groove wall of each groove 472 defines a first plane 474 and a first inclined surface 476 opposite to the first plane 474.

The lower jaw 48 has a shaft portion 49 vertically movably inserted into the support base 20, a lower clamping portion 50 formed integrally with the top end of the shaft portion 49 and disposed outside the support base 20, and a slope 51 located on an opposing bottom end of the shaft portion 49 and abutted against the slope 46 of the slide 44 (see FIG. 6a) for pushing the lower jaw 48 upward upon horizontal displacement of the slide 44.

The locking unit 60 comprises a stop block 61, a return spring 64, a locking bar 66, and a linkage rod 71.

The stop block 61 is vertically movably mounted to the support base 20, having a second positioning portion 62 located on a top surface thereof. In this embodiment, as shown in FIG. 9, the second positioning portion 62 is formed by a plurality of bumps 622 arranged at equal intervals and respectively coupled to the grooves 472. Each bump 622 has a second plane 624 and an opposing second inclined surface 626. The second planes 624 and second inclined surfaces 626 of the bumps 622 are respectively abutted with the first planes 474 and first inclined surfaces 476 of the grooves 472. Thus, the second positioning portion 62 of the stop block 61 cooperates with the first positioning portion 47 of the slide 44. The stop block 61 further has an extension portion 63 inserted into the opening 25 of the back baffle 23. Further, the size of the extension portion 63 of the stop block 61 is smaller than the size of the opening 25 of the back baffle 23 so that the stop block 61 and the back baffle 23 do not interfere with each other during vertical displacement of the stop block 61.

The return spring 64 (here is a compression spring) has the opposing top and bottom ends thereof respectively stopped against the bottom surface of the stop block 61 and the top surface of a bearing plate 65. The bearing plate 65 is affixed to the front baffle 21 by using fastening members such as screws. Thus, the return spring 64 provides a spring force to push the stop block 61 toward the slide 44.

Figure 5:
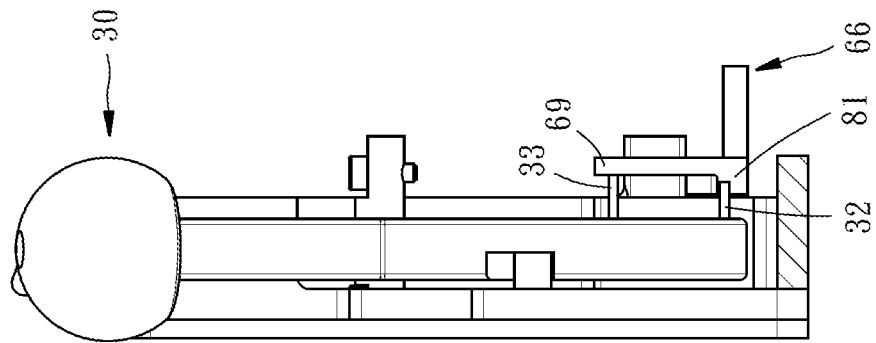
FIG. 5 is a side view of a part of the clamping device, showing the relative position between the first lateral portion of the handle and the pushing portion of the locking bar.
Figure 4:
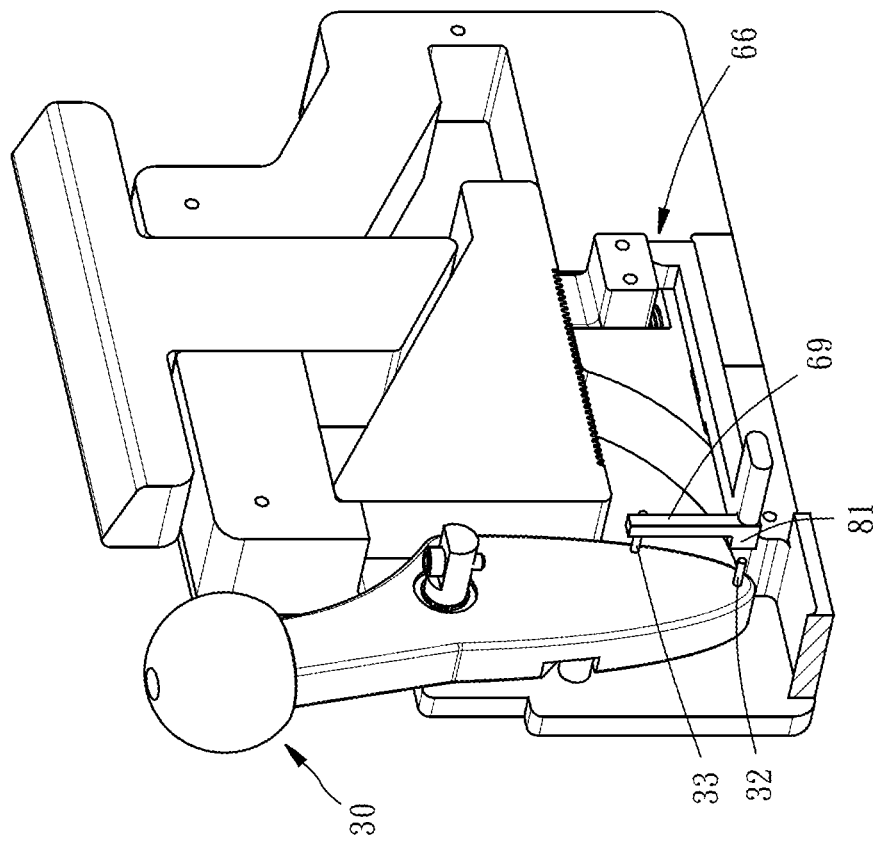
FIG. 4 is an elevational view of a part of the clamping device, showing the relative position between the first lateral portion of the handle and the pushing portion of the locking bar.

The locking bar 66 is horizontally movably mounted in the support base 20, having a position-limiting portion 67 located in the middle and coupled to the position-limiting groove 67 of the front baffle 21, a locking portion 68 located at one end thereof and disposed below the extension portion 63 of the stop block 61, an upright portion 69 located at an opposite end thereof, and a dial portion 70 and a pushing portion 81 respectively disposed perpendicular to the upright portion 69 (see FIGS. 4 and 5). The dial portion 70 of the locking bar 66 is inserted through the elongated slot 24 of the back baffle 23 and protrudes from the outer side of the back baffle 23 (i.e., one side of the support base 20 back to a side rail 12, as shown in FIG. 1).

The linkage rod 71 is abutted against the outer side of the back baffle 23 (i.e., the side of the support base 20 back to the side rail 12, as shown in FIG. 1), having a mounting portion 74 located at one end thereof and affixed to the extension portion 63 of the stop block 61 by using fastening members such as screws for allowing the linkage rod 71 and the stop block 61 to move synchronously, and a protrusion 72 located at an opposite end thereof and abutted against the dial portion 70 of the locking bar 66 to work as a secondary security mechanism.

Figure 6B:
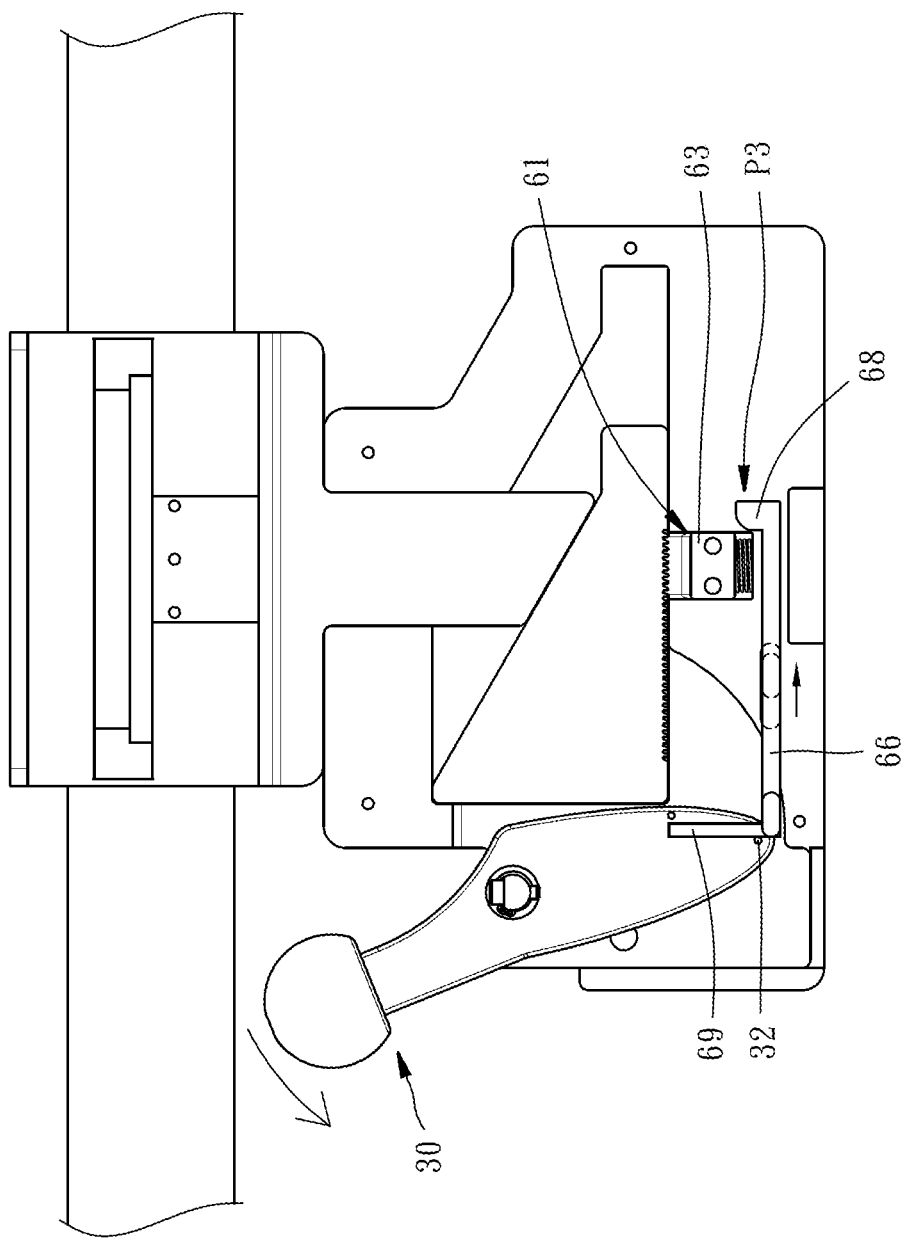
Figure 6D:
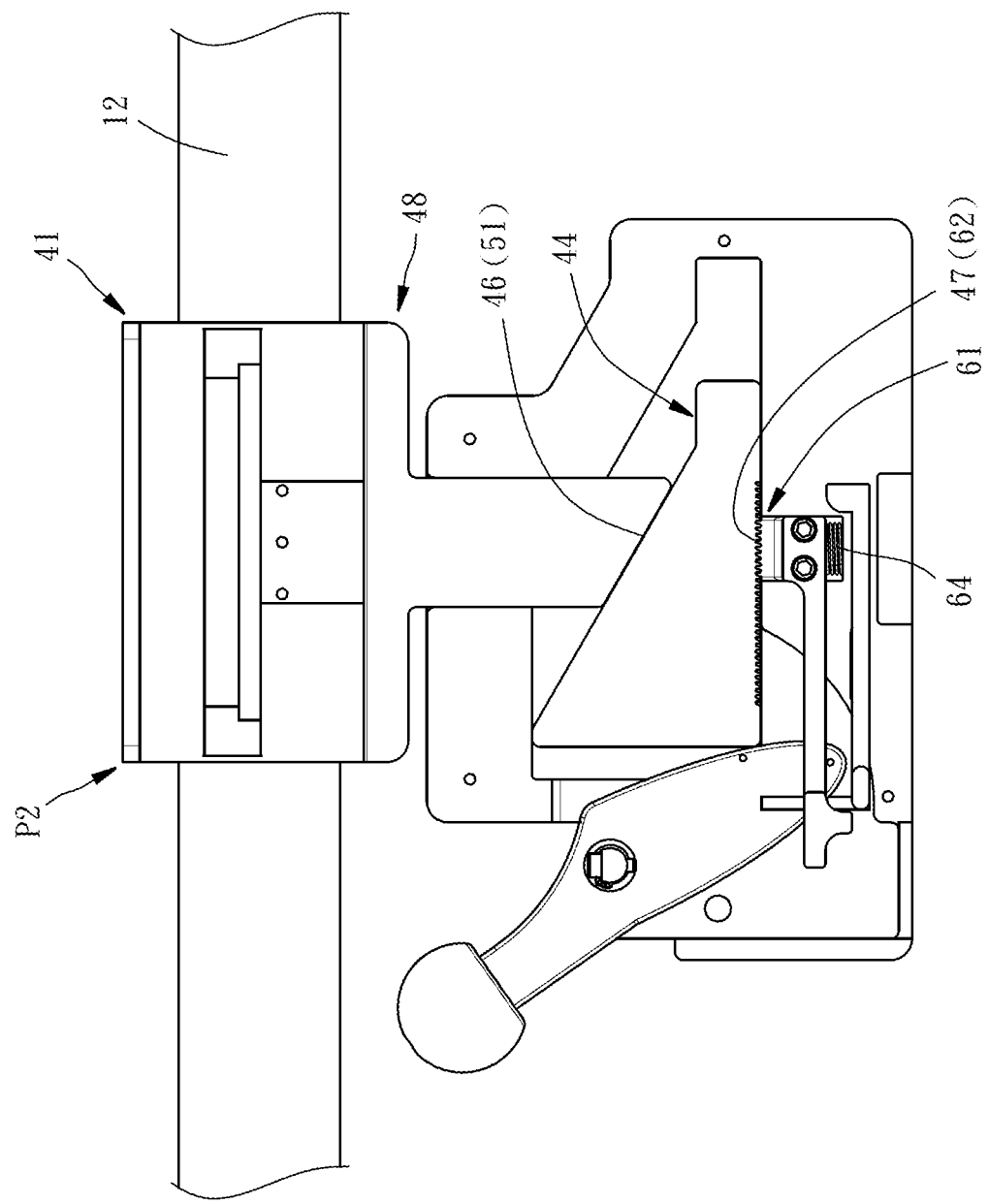
Figure 6E:
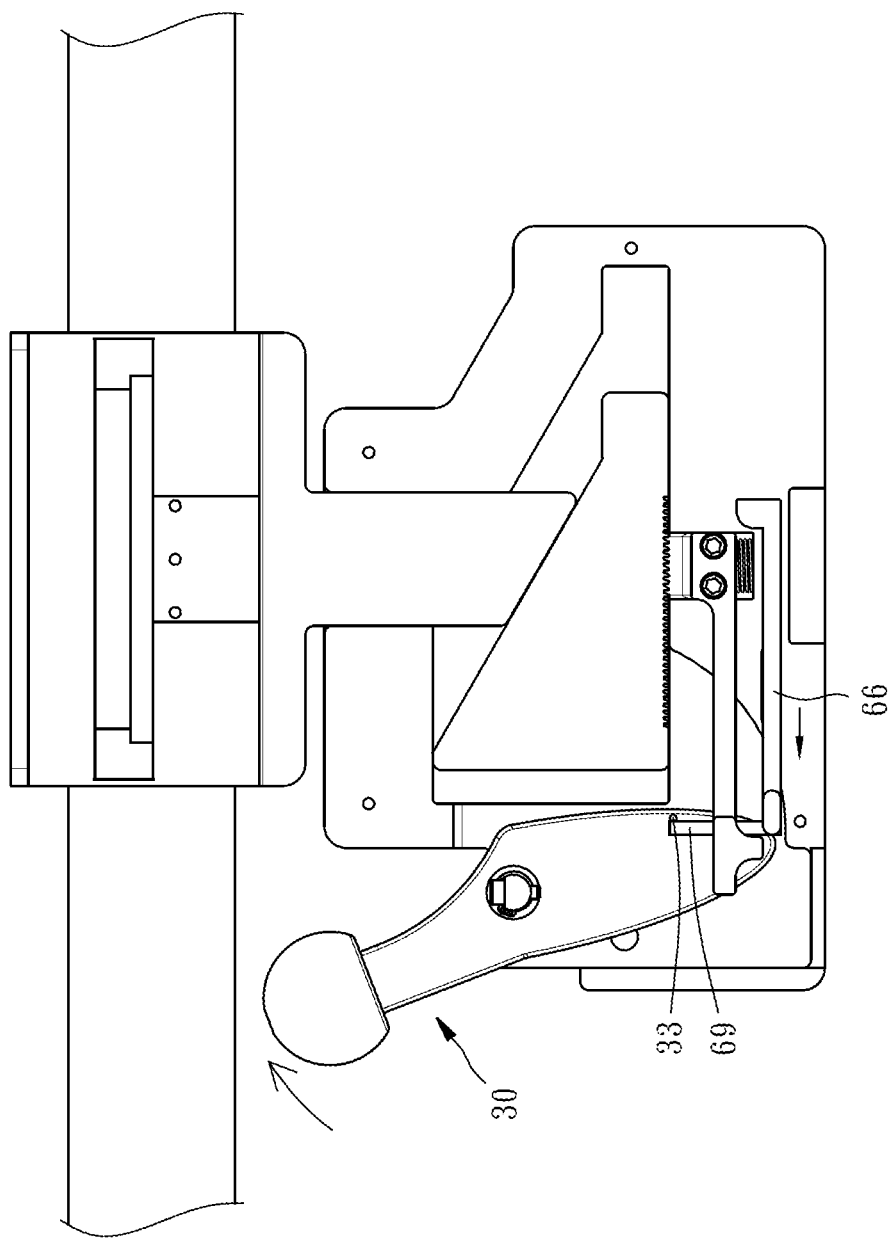
Figure 6F:
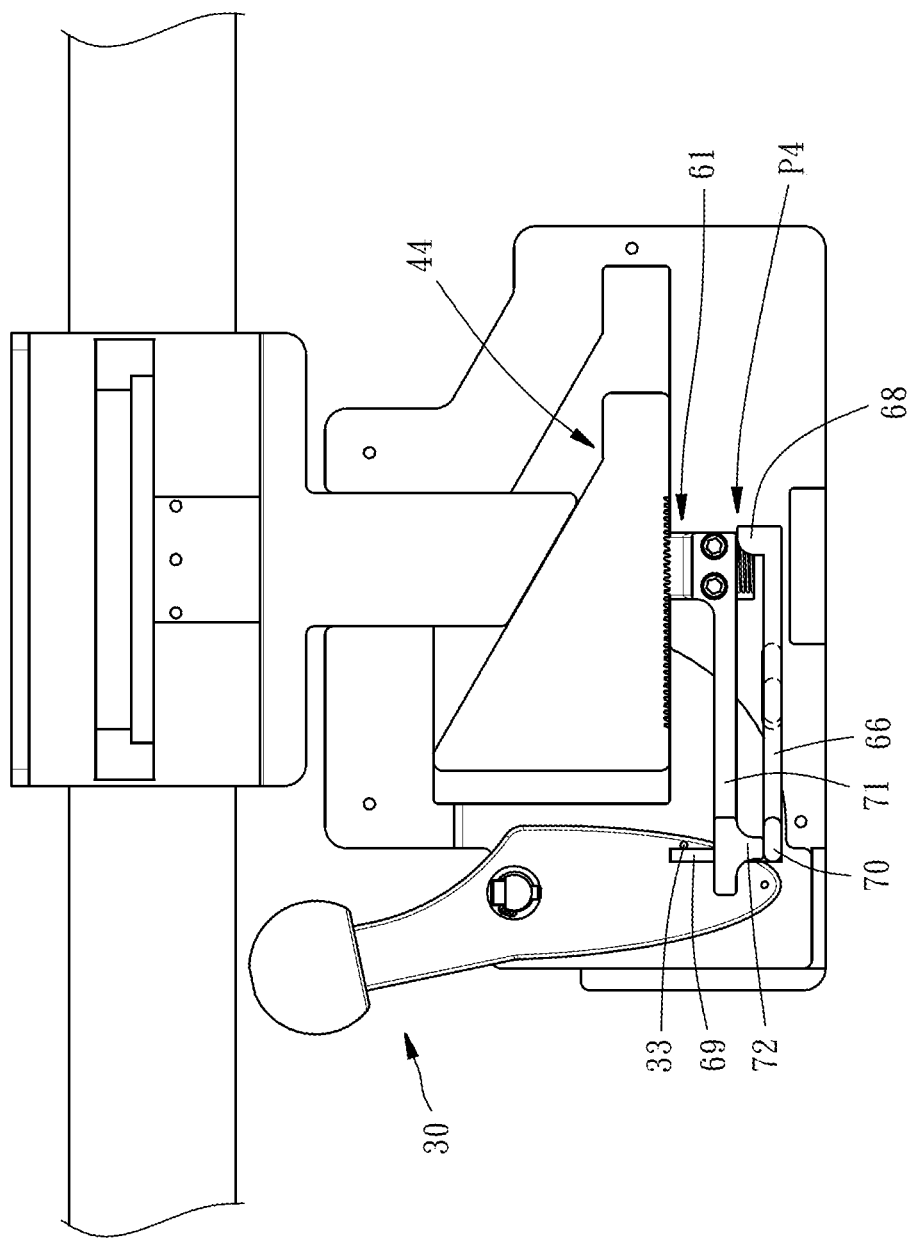
Figure 8:
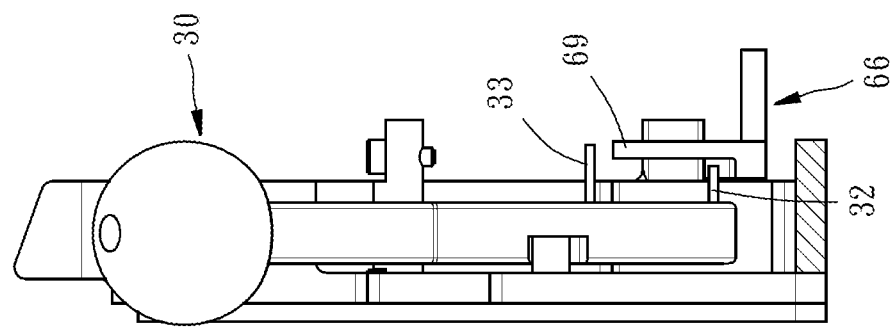
FIG. 8 is a side view of a part of the clamping device, showing the relative position between the first lateral portion of the handle and the upright portion of the locking bar.

In actual installation, first rotate the handle 30 to drive the handle 30 to push the pushing portion 81 of the locking bar 66 with the first lateral portion 32, causing the locking bar 66 to move to the right. Since the handle 30 is turned about the pivot axle 35, the first lateral portion 32 will then be separated from the pushing portion 81. Thereafter, as shown in FIGS. 6a and 6b (for convenience of explanation, the linkage rod 71 is omitted in FIG. 6), when the locking portion 68 of the locking bar 66 is staggered from the extension portion 63 of the stop block 61, the locking bar 66 reaches the unlocking position P3. At this time, the stop block 61 can be actuated up and down. Then continue to push the handle 30 to the left, at this time because the first lateral portion 32 of the handle 30 has a relatively short relationship in length, as shown in FIGS. 7 and 8, the first lateral portion 32 of the handle 30 does not touch the upright portion 69 of the locking bar 66 to avoid mutual interference during the continuous pivoting of the handle 30. Then the handle 30 starts to push the bearing plane 45 of the slide 44 with the arched push surface 34. At this time, because the stop block 61 is in a state in which it can be moved up and down, the slide 44 is driven to move to the right, as shown in FIGS. 6c and 6d. During the movement of the slide 44, on the one hand, the first plane 474 of the first positioning portion 47 pushes the second plane 624 of the second positioning portion 62 of the stop block 61, causing the stop block 61 to alternatively move up and down under the dual action of slide 44 and return spring 64. On the other hand, the slope 46 pushes the slope 51 of the lower jaw 48, so that the lower jaw 48 is pushed up from the release position P1 (as shown in FIG. 6a) to the clamp position P2 (as shown in FIG. 6d). Until the lower jaw 48 reaches the clamping position P2, the side rail 12 of an operating bed is clamped between the upper jaw 41 and the lower jaw 48. Then push the handle 30 to the right to cause the handle 30 to push the upright portion 69 of the locking bar 66 with the second lateral portion 33, as shown in FIG. 6e. At this time, because the second lateral portion 33 of the handle 30 has a relatively long relationship in length, during the reverse pivoting of the handle 30, the second lateral portion 33 of the handle 30 continues to contact the upright portion 69 of the locking bar 66, causing the locking bar 66 to continuously move to the left to the extent where the locking portion 68 and dial portion 70 of the locking bar 66 are respectively abutted against the extension portion 63 of the stop block 61 and the protrusion 72 of the linkage rod 71, as shown in FIG. 6f. At this time, the locking bar 66 reaches the locking position P4, so that the stop block 61 cannot be moved up and down. At this time, the slide 44 is positioned by the stop block 61 and cannot be moved, so the installation is completed.

Figure 2:
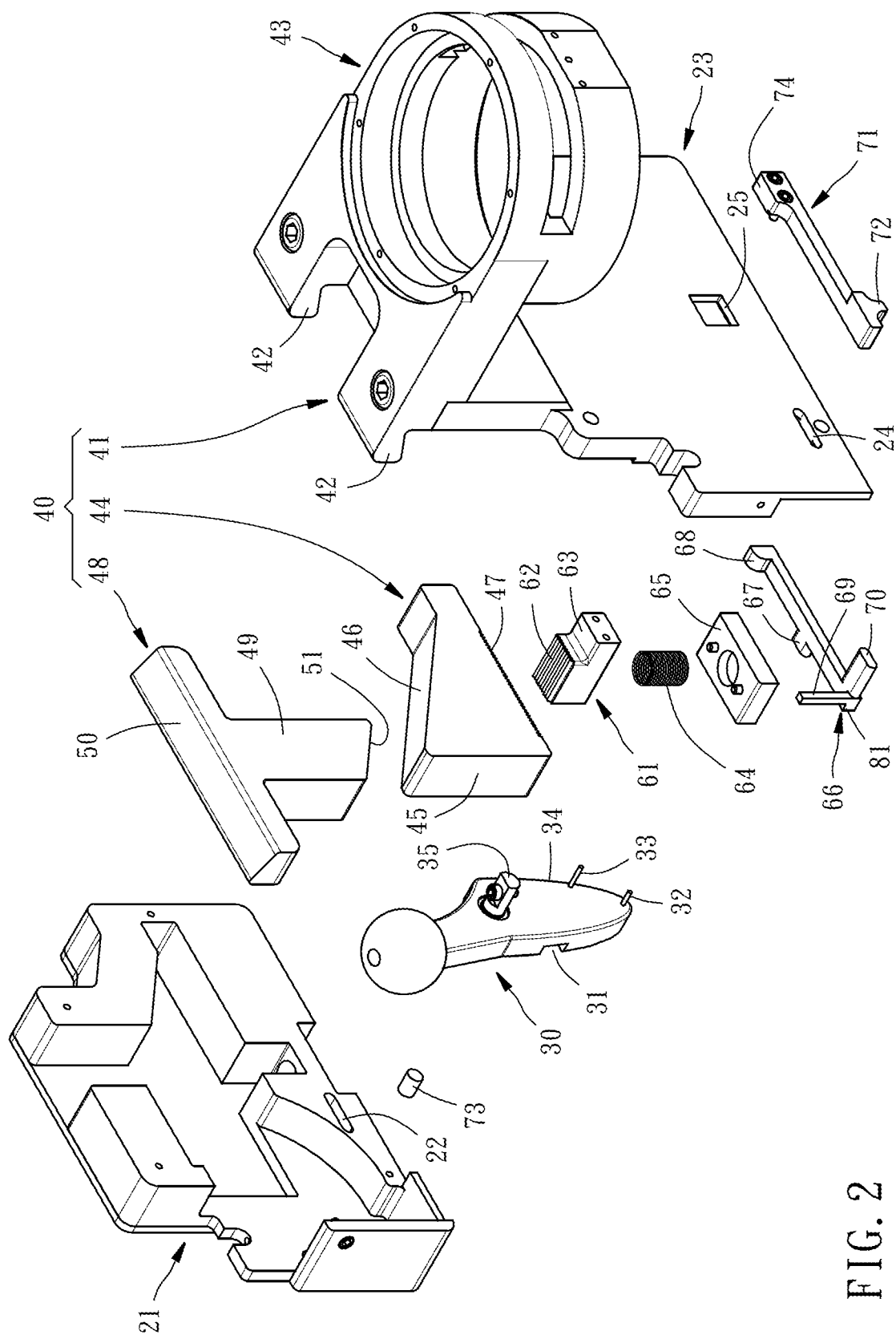
FIG. 2 is an exploded view of the clamping device in accordance with the present invention.
Figure 3:
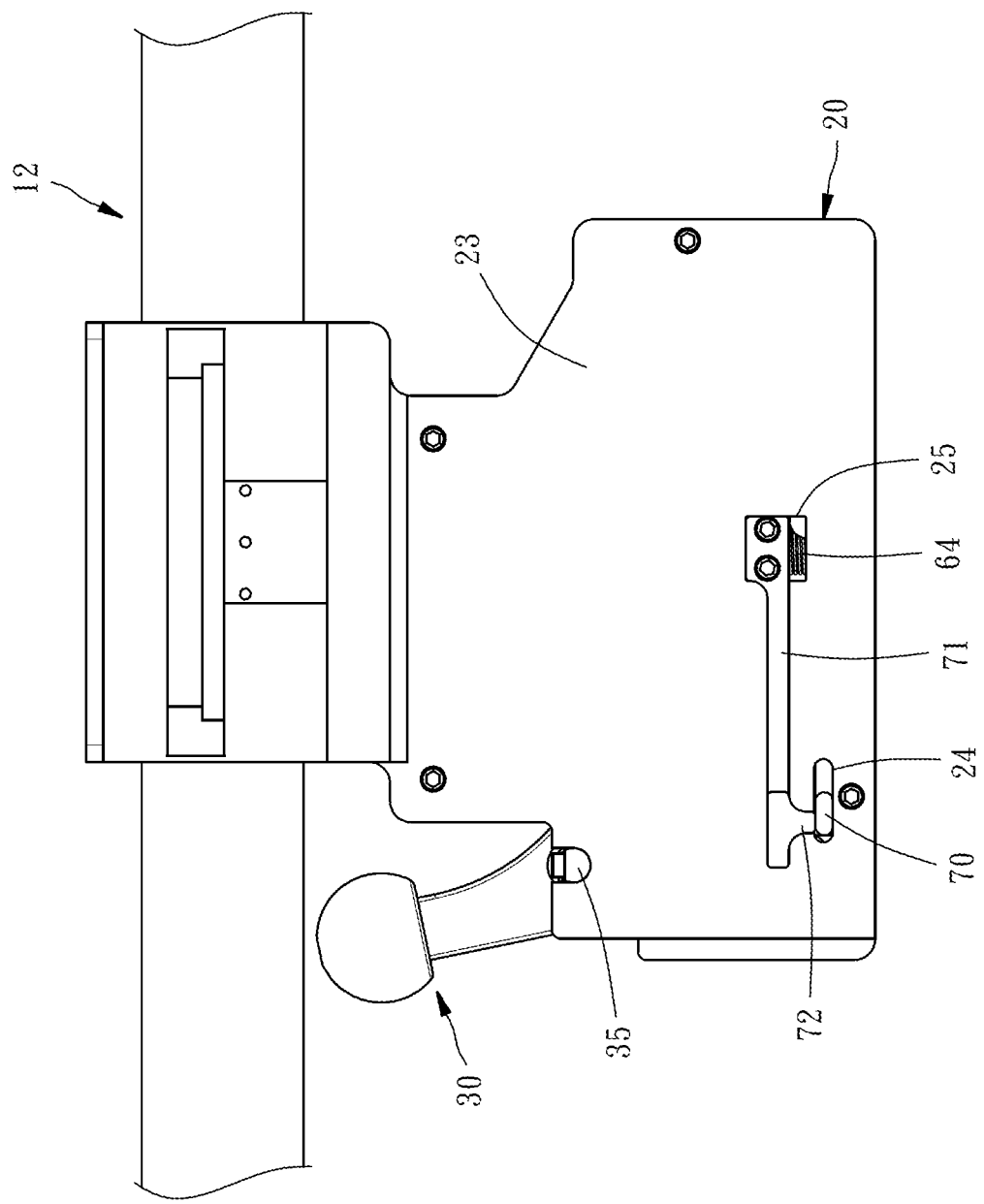
FIG. 3 is a plain view of the clamping device in accordance with the present invention.

However, in order to avoid malfunction of the handle 30, a magnet 73 is mounted at an inner side of the front baffle 21 (see FIG. 2). When the handle 30 is in the initial state as shown in FIG. 6a, the handle 30 will be engaged with the magnet 73 by the notch 31, so that the handle 30 is attracted and positioned by the magnet 73. After the installation is completed, the axial direction A of the pivot axle 35 and the outer side 14 of the side rail 12 extend perpendicularly to each other, so that the operation direction of the handle 30 can be prevented from interfering with the surrounding person or object.

Figure 6G:
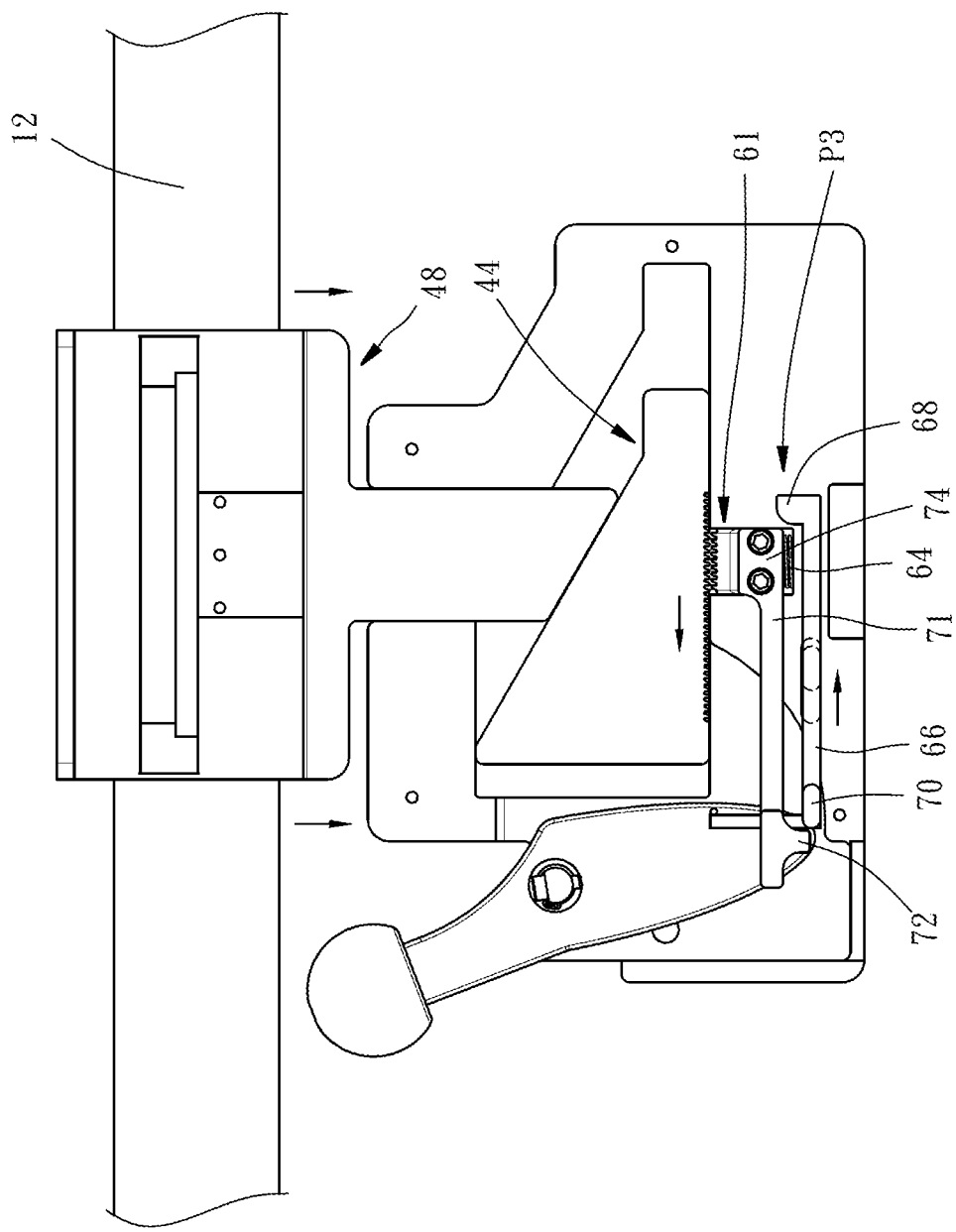
Figure 7:
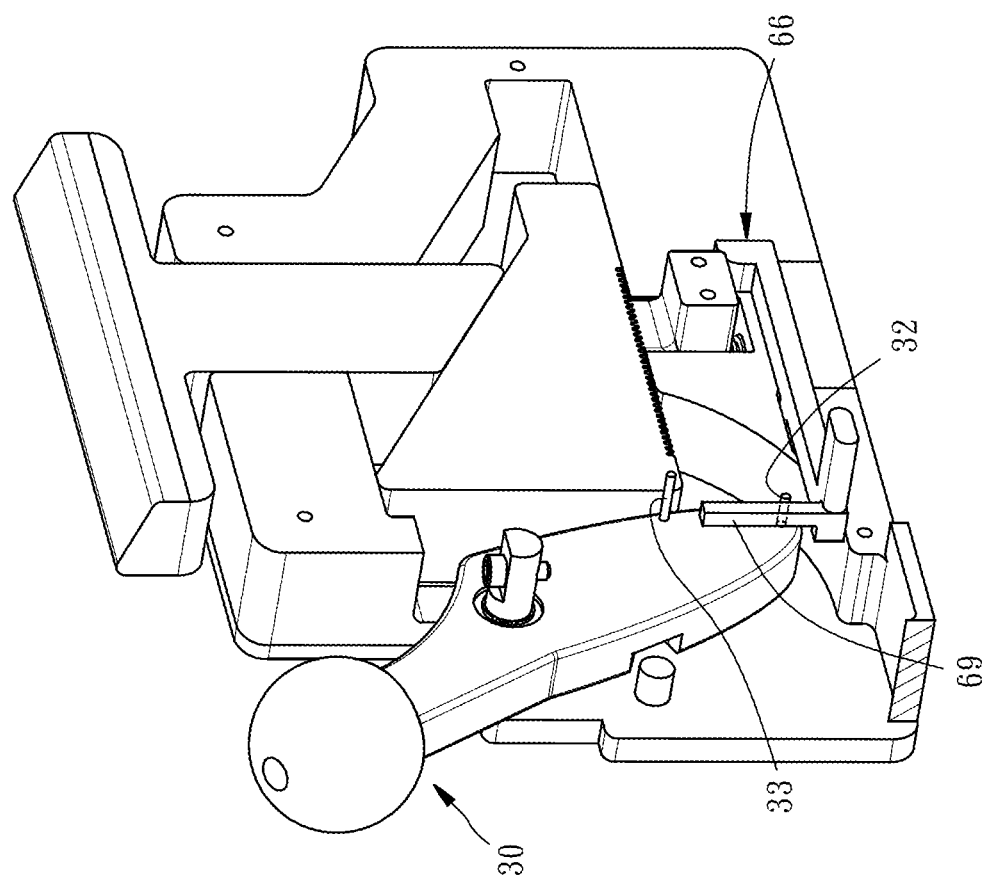
FIG. 7 is an elevational view of a part of the clamping device, showing the relative position between the first lateral portion of the handle and the upright portion of the locking bar.

When disassembling, the dial portion 70 of the locking bar 66 is biased to the right with one hand, as shown in FIG. 6g, on the one hand, the dial portion 70 of the locking bar 66 is removed from the protrusion 72 of the linkage rod 71, on the other hand, the locking portion 68 of the locking bar 66 is removed from the extension portion 63 of the stop block 61, that is, the locking bar 66 is moved to the unlocking position P3. Then, press down the mounting portion 74 of the linkage rod 71 with one hand. Since the mounting portion 74 of the linkage rod 71 is fixed with the extension portion 63 of the stop block 61, the stop block 61 will be moved downward synchronously. Thus, the stop block 61 compresses the return spring 64 and unlocks the slide 44. The user then holds the mounting seat 43 and applies upward force. With the side rail 12 in contact with the upper jaw 41 and the lower jaw 48, the side rail 12 is applied to the lower jaw 48 and the slide 44 is pushed to the left until the lower jaw 48 is lowered to the release position P1, as shown in FIG. 6a. At this time, the side rail 12 is released for disassembly.

Figure 10:
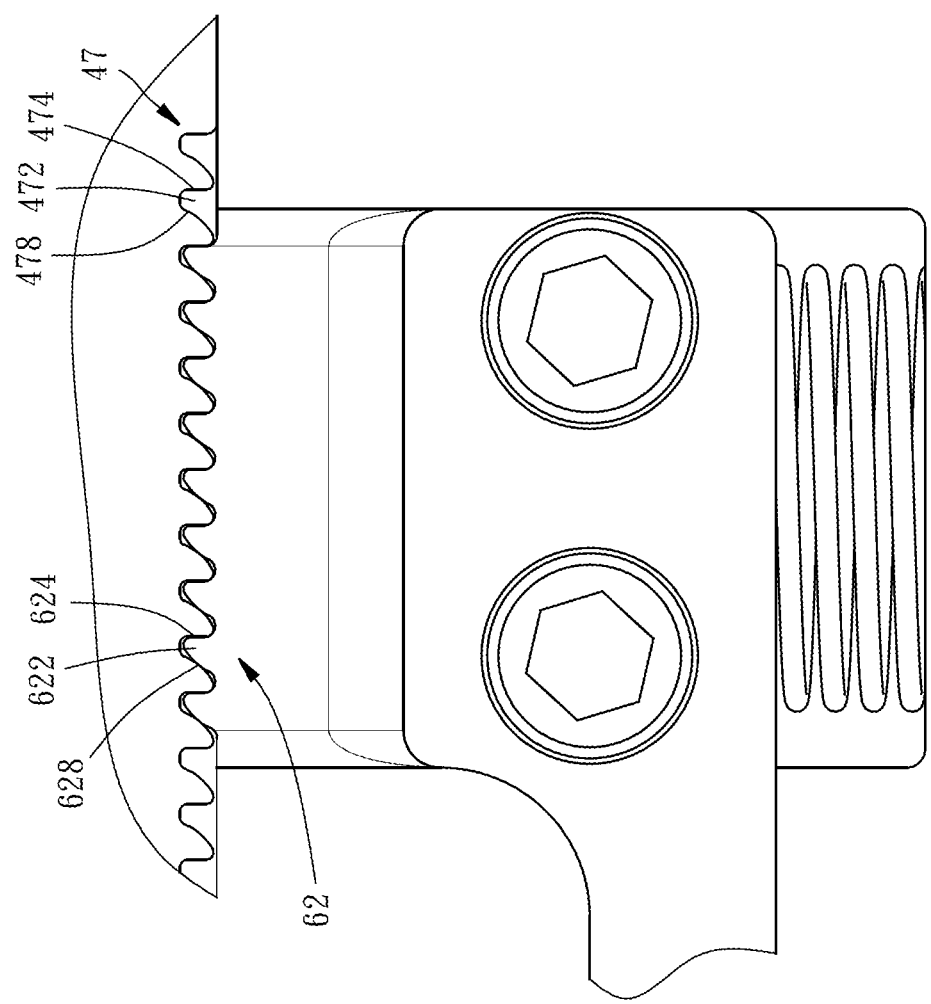
FIG. 10 is similar to FIG. 9, showing an alternate form of the first positioning portion of the slide and the second positioning portion of the stop block.

It should be added here that there may be different structural changes between the grooves 472 of the slide 44 and the bumps 622 of the stop blocks 61. As illustrated in FIG. 10, each groove 472 of the slide 44 has a first plane 474 and an opposing first curved surface 478, and each bump 622 of the stop block 61 has a second plane 624 and an opposing second curved surface 628. The first planes 474 of the grooves 472 of the slide 44 are respectively abutted against the second planes 624 of the bumps 622, and the first curved surfaces 478 of the grooves 472 of the slide 44 are respectively abutted against the second curved surfaces 628 of the bumps 622. Thus, the first positioning portion 47 of the slide 44 and the second positioning portion 62 of the stop block 61 can also utilize the cooperation between each other to produce a positioning effect.

In conclusion, the clamping device 10 of the present invention is installed and disassembled with one hand and has a safety mechanism to avoid accidental loosening caused by accidental contact by others, thereby achieving rapid positioning, convenient disassembly and application safety.

What is claimed is:

1. A clamping device for attaching a surgical auxiliary device to one side rail of an operating bed, comprising:
 a support base;
 a handle pivotally mounted to said support base;
 a clamping unit comprising an upper jaw, a slide and a lower jaw, said upper jaw being affixed to a top surface of said support base, said slide being mounted in said support base and horizontally movable relative to said support base by said handle, said slide comprising a first positioning portion and a slope, said lower jaw being vertically movably mounted to said support base and comprising a slope, the said slope of said lower jaw being abutted against the said slope of said slide so that said lower jaw is upwardly movable by said slide from a release position to a clamping position where said side rail is clamped between said upper jaw and said lower jaw; and
 a locking unit comprising a stop block, a return spring and a locking bar, said stop block being vertically movably mounted in said support base and comprising a second positioning portion, said second positioning portion of said stop block incorporating said first positioning portion of said slide, said return spring acting on said stop block to push said stop block toward said slide, said locking bar being horizontally movably mounted in said support base and movable by said handle relative to said stop block between a locking position where a locking portion of said locking bar pushes said stop block to hold said slide in position and an unlocking position where said locking portion of said locking bar is released from said stop block for allowing said slide to be displaced horizontally.

2. The clamping device as claimed in claim 1, wherein said side rail has an outer surface; said handle is pivotally connected to said support base with a pivot axle, an axial direction of said pivot axle being perpendicular to an extending direction of said outer surface of said side rail.

3. The clamping device as claimed in claim 1, wherein said slide comprises a bearing plane; said handle comprises an arched push surface adapted for pushing said bearing plane of said slide to cause said lower jaw to move upwardly from said release position to said clamping position.

4. The clamping device as claimed in claim 1, wherein said handle comprises a first lateral portion and a second lateral portion respectively located on one side thereof, a length of said first lateral portion being less than a length of said second lateral portion, a position of said first lateral portion being lower than a position of said second lateral portion; said locking bar has said locking portion located at one end thereof and an upright portion and a pushing portion located at an opposite end thereof, said pushing portion of said locking bar being adapted for pushing by said first lateral portion of said handle to cause movement of said locking bar from said locking position toward said unlocking position, said upright portion of said locking bar being adapted for pushing by said second lateral portion of said handle to cause movement of said locking bar from said unlocking position toward said locking position.

5. The clamping device as claimed in claim 1, wherein said support base comprises a position-limiting groove; said locking bar comprises a position-limiting portion horizontally movably coupled to said position-limiting groove of said support base.

6. The clamping device as claimed in claim 1, wherein said support base comprises an elongated slot; said locking bar comprises an upright portion and a dial portion located at one end thereof, said dial portion being perpendicular to said upright portion and horizontally movably inserted through said elongated slot of said support base and protruding from one side of said side rail back to said support base.

7. The clamping device as claimed in claim 6, wherein said support base further comprises an opening; said stop block comprises an extension portion engaged into said opening of said support base; said locking unit further comprises a linkage rod stopped against one side of said support base opposite to said side rail, said linkage rod having one end thereof affixed to said extension portion of said stop block and an opposite end thereof provided with a protrusion, said protrusion of said linkage rod being pushed by said dial portion of said locking bar when said locking bar is in said locking position, said protrusion of said linkage rod being released from said dial portion of said locking bar when said locking bar is in said unlocking position.

8. The clamping device as claimed in claim 1, wherein said support base has a magnet mounted therein; said handle comprises a notch; said handle is attracted and positioned by said magnet when said magnet is engaged in said notch of said handle.

9. The clamping device as claimed in claim 1, wherein said clamping unit further comprises a mounting seat connected to said upper jaw for the mounting of said surgical auxiliary device.

10. The clamping device as claimed in claim 1, wherein said first positioning portion of said slide is constructed of a plurality of grooves arranged at equal intervals; said second positioning portion of said stop block is constructed of a plurality of bumps arranged at equal intervals and respectively coupled to said grooves of said first positioning portion of said slide.

* * * * *